United States Patent [19]

Sun

[11] 4,079,087

[45] Mar. 14, 1978

[54] THREE PHASE CRYSTALLIZATION OF BISPHENOL A

[75] Inventor: Yun Chung Sun, Midland, Mich.

[73] Assignee: The Dow Chemical Company, Midland, Mich.

[21] Appl. No.: 794,375

[22] Filed: Jan. 27, 1969

[51] Int. Cl.$^2$ .............................................. C07C 37/22
[52] U.S. Cl. ........................... 260/619 A; 260/515 A; 260/521 B; 260/525; 260/612 R; 260/620; 260/621 A; 260/622 R; 260/622 P; 260/649 R; 260/650 R; 260/674 A; 260/674 N; 260/674 SE; 260/675
[58] Field of Search ..................................... 260/619 A

[56] References Cited

U.S. PATENT DOCUMENTS

| | | | |
|---|---|---|---|
| 1,978,949 | 10/1934 | Kohn et al. | 260/619 A X |
| 2,959,622 | 11/1960 | Grimme et al. | 260/619 A |
| 3,383,425 | 5/1968 | Mansfield | 260/619 A |
| 3,535,389 | 10/1970 | De Jong | 260/619 A |

*Primary Examiner*—Norman Morgenstern
*Attorney, Agent, or Firm*—Glwynn R. Baker

[57] ABSTRACT

A process for purifying a crude crystalline or crystallizable water-immiscible aromatic compound contaminated with one or more related congeneric impurities which cannot be readily separated by distillation, said process comprising:

1. forming a dispersion of liquefied crude material in an aqueous liquid by agitating the mixture;
2. effecting crystallization of the desired aromatic compound while maintaining the dispersion;
3. reducing agitation sufficiently to permit the formation of three phases, i.e., a solid crystalline phase, an aqueous liquid phase, and a mother liquor phase; and
4. separating the crystals;

said aqueous liquid being immiscible with, and having a density between, the aforementioned solid crystalline phase and the mother liquor phase.

1 Claim, No Drawings

THREE PHASE CRYSTALLIZATION OF BISPHENOL A

BACKGROUND OF THE INVENTION

Congeneric, close-boiling mixtures of aromatic compounds cannot always be separated into their components by distillation. Usually their solubility characteristics are so closely related that selective extraction of the components is not feasible. Selective crystallization from special solvents usually requires one or more recrystallization steps to reduce the concentration of contaminants to an acceptable level, and solvent washing requires large amounts of solvent. Also, these two procedures are relatively expensive because recoveries of the desired product are generally fairly low and the cost of solvent purification, and/or discarding of contaminated solvent, is high. Generally conversion of contaminants to derivatives which are readily separated from the final mixture is not feasible because the desired product also tends to react in a manner similar to the contaminants. In fact, the source of the contaminants in the congeneric mixture is usually a chemical reaction which cannot be controlled with the degree of specificity needed to obtain an end product of desired purity.

SUMMARY OF THE INVENTION

The instant invention is a process for purifying a crude crystalline or crystallizable aromatic compound contaminated with one or more related congeneric impurities which cannot be readily separated by distillation, said process comprising:

1. forming a dispersion of liquefied crude material in an aqueous liquid by agitating a mixture of the two;
2. effecting crystallization of the desired aromatic compound while maintaining the dispersion;
3. reducing agitation sufficiently to permit the formation of three phases, i.e., a solid crystalline phase, an aqueous liquid phase, and a mother liquor phase; and
4. separating the crystals;

said aqueous liquid being immiscible with, and having a density between, the aforementioned solid crystalline phase and the mother liquor phase.

The contaminants contemplated by the method of this invention include those which are close-boiling, i.e., have boiling points sufficiently close to the desired compound so that separation by normal techniques of distillation is impossible or impractical, especially congeneric impurities, i.e., closely-related compounds such as homologs, analogs and isomers which are produced generally in the same reaction that forms the desired compound, or are present when a common source such as petroleum oil, or a fraction thereof, is treated.

Suitably the compound to be purified should represent at least about 25% of the mixture to be purified by the process of this invention. While mixtures containing greater amounts of impurities can be purified, it is to be noted that the instant invention is a highly desirable method for removing small or trace amounts (i.e., 10% or less) of impurities which are difficult or impossible to separate by methods heretofore available.

Representative aromatic compounds which are generally obtainable in pure crystalline form, and which are immiscible with the aqueous liquid, therefore being contemplated by the method of this invention, generally contain from 1 to 3 aromatic rings and suitably include: (I) aromatic hydrocarbons, such as benzene, naphthalene, anthracene and phenanthrene; (II) alkyl-, alkenyl- and alkynyl-substituted aromatic hydrocarbons, such as toluene, xylene (o-, m- and p-), hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, methylnaphthalene (1- and 2-), dimethylnaphthalene (1,4- and 2,3-), styrene, phenylacetylene and stilbene (trans- and cis-); (III) aromatic carboxylic acids, such as benzoic, phthalic, isophthalic, terephthalic, pyromellitic (and the anhydrides thereof), naphthoic ($\alpha$ and $\beta$); (1) alkylsubstituted aromatic carboxylic acids, such as toluic (o-, m- and p-); (2) hydroxyl-substituted aromatic carboxylic acids, such as hydroxybenzoic acid (o-, m- and p-); (3) halogen-substituted aromatic carboxylic acids, such as chloro- and bromobenzoic acids; (IV) hydroxyl-substituted aromatics, such as phenol, catechol, resorcinol, hydroquinone, naphthol ($\alpha$ and $\beta$); (1) alkyl-substituted hydroxyaromatics, such as cresol (o-, m- and p-); (2) nitro-substituted hydroxyaromatics, such as nitrophenol (o-, m- and p-), dinitrophenol and trinitrophenol; (V) bisphenols, such as bisphenol A (4,4'-isopropylidenediphenol) and halogenated bisphenols, such as chlorinated and brominated bisphenol A; (VI) halogen-substituted aromatics, such as bromo-, chloro-, fluoro-, and iodobenzene, bromochlorobenzene (1,2-, 1,3-, and 1,4-), dichlorobenzene, trichlorobenzene, tetrachlorobenzene; and $\alpha$- and $\beta$- chloro- and -bromonaphthalene; (VII) phenyl-substituted aromatics, such as biphenyl; (1) alkyl-substituted phenylaromatics such as methylbiphenyl (2-, 3-, and 4-); (2) hydroxysubstituted phenylaromatics, such as o-, m- and p-phenylphenol; (VIII) diphenylmethane; and (IX) diphenyl oxide.

The compounds suitable for purification by the process of this invention also can be, but are not necessarily, the contaminants to be removed in particular cases. As stated above, the congeneric contaminants contemplated by this invention often are isomers, homologs and analogs of the desired compound.

The crude material can suitably be liquefied by melting it alone or with a small amount of added solvent. Solvents which are suitable for this are generally those useful for the recrystallization of the particular product. For instance, alcohols such as the butanols, n-amyl alcohol and n-hexyl alcohol are suitable. Also suitable are aromatic hydrocarbons such as benzene, toluene, the xylenes and their derivatives; aliphatic hydrocarbons such as n-pentane, n-hexane, n-heptane, n-octane and their derivatives.

The aqueous liquid utilized in the practice of this invention should be (1) substantially immiscible with both the desired crystalline product and the mother liquor; and (2) have a density between them. Suitable examples include water and aqueous solutions of inert, water soluble materials, such as NaCl, $NH_3$, $CaCl_2$, $(NH_4)_2SO_4$ and $(NH_4)_3PO_4$.

Suitable amounts of the aqueous liquid should be employed to form an aqueous phase sufficient in height to completely separate the crystalline and mother liquor phases, thereby preventing the mother liquor from recontacting and contaminating the crystals during separation of the phases.

It is essential to the process of the invention that the liquefied crude material (organic phase) be finely dispersed in the aqueous liquid phase during crystallization. However, it is to be noted that the dispersion is not to be so fine as to amount to an emulsion.

The dispersion can be effected by, for instance, agitation, resulting from mechanical means such as stirrers, shakers, and other well-known means.

Crystallization can be effected by conventional methods, such as cooling to the freezing point of the desired material, or, when a solvent is present, cooling and/or evaporating sufficient solvent to cause crystallization.

After crystallization is complete, agitation should be reduced to allow three phases (crystals, mother liquor and aqueous liquid) to form. This process can be accelerated by centrifugation. After the phases have formed and become distinguishable, the crystals can be separated by several methods, including decanting off the mother liquor and then removing the aqueous liquid that is left from the crystals by filtration. Separation methods are suitable which do not contact the crystals with the mother liquor.

Advantages of the instant method over those currently known to the art include:

(1) The crystals formed in the presence of the aqueous liquid contain less trapped impurities than those crystallized from mother liquor only, eliminating the need for further recrystallization;

(2) The crystals so formed are more uniform in size, and generally finer than those formed by conventional crystallization techniques;

(3) If a solvent is needed to place the contaminants in solution, a minimal amount can be used, without concern as to material-handling problems, since the aqueous phase maintains fluidity.

SPECIFIC EMBODIMENTS

Example 1

Crude crystalline material (45 g. of biphenyl in (a)-(c), and 40 g. of naphthalene in (d)-(f)), a solvent and deionized water were placed in 4 oz. bottles, the recipes being listed in Table I below. The bottles were then placed in an oven and heated until all the solid melted (70° C. for Examples (a)-(c), and 80° C. for Examples (d)-(f)). They were then mounted in a shaker and agitated for 3 hours in the case of (a)-(c), and 2 hours for (d)-(f), during which the systems cooled to room temperature and came to equilibrium. The contents of each bottle were then centrifuged, resulting in separation into three phases (crystals, water and mother liquor).

The crude biphenyl was contaminated with naphthalene, methylnaphthalenes, diphenylmethane and methylbiphenyls. The crude naphthalene was contaminated with methylnaphthalenes, propylbenzene, methylstyrene, indene and methyl and dimethyl indenes.

Identical samples and procedures (a) to (f) were repeated, but without adding water. These samples were merely crystallized by conventional methods and analyzed (see column marked "without water-purity").

The data are contained in Table I below:

Example 2

75 ml. of p-xylene, 10 ml. of m-xylene, 1 ml. of o-xylene, 1 ml. of ethylbenzene and 20 ml. of deionized water were placed in a 4 oz. bottle. The bottle was mounted in a shaker, and the entire apparatus placed in a refrigeration unit at a temperature of about 0° C. for approximately one hour, with continuous agitation, at which time the system had reached equilibrium.

After centrifugation, at about 0° C., the p-xylene (initial purity 86 wt. percent) had a purity of 99+ wt. percent, with a recovery of 56 wt. percent.

Example 3

50 g. of crude crystalline p-dichlorobenzene (99.30 wt. %), containing 0.35 wt. % of m- and 0.33 wt. % of o- isomers, and 0.02 wt. % of chlorotoluene, 15 ml. of n-butanol and 45 ml. of deionized water were placed in a 4 oz. bottle. The bottle was placed in an oven (50° C.) and heated until all the solid melted. It was then mounted in a shaker and agitated at room temperature (28° C.) for approximately 1 hour, at which time the system had reached equilibrium.

After centrifugation the p-dichlorobenzene had a purity of 99.97 wt. %, with a recovery of 82 wt. %.

Example 4

40 g. of crude crystalline bisphenol A (97.66 wt. %), containing 1.7 wt. % of o,p'-isopropylidene-diphenol, 0.6% trisphenol and 0.04% phenol, and 50 ml. of deionized water were placed in a 4 oz. bottle. The bottle was placed in an oven (97° C.) and heated until all the solid melted. 50 ml. of chlorobenzene and 12 g. NaCl (resulting in a 20% aqueous solution) were then added, the bottle placed in a shaker and agitated at room temperature (28° C.) for approximately one hour, at which time the system had reached equilibrium.

After centrifugation, the bisphenol A had a purity of 99.70 wt. %, with a recovery of 90 wt. %.

I claim:

1. A process for purifying a crude bisphenol A compound from a mixture containing at least 25 weight percent of said compound, contaminated with one or more related cogeneric impurities which cannot be readily separated by distillation, said process comprising:
    1. forming a dispersion of liquefied crude bisphenol A in chlorobenzene in an inert immiscible aqueous 20% solution of sodium chloride by agitating a mixture of the two wherein said aqueous liquid is substantially immiscible with both the bisphenol A, and the mother liquor phase composed of the liquid impurities and chlorobenzene containing the liquid impurities, and the said aqueous liquid has a density between (a) and (b),
    2. effecting crystallization of the bisphenol to be purified while maintaining the dispersion;

TABLE I

| Ex. No. | Purity* Initial | Final | Recovery* | Solvent | Solvent (ml.) | H₂O (ml.) | Without H₂O-Purity* |
|---|---|---|---|---|---|---|---|
| (a) | 94.5 | 99.4 | 75 | Toluene | 15 | 40 | 96.1 |
| (b) | 96.0 | 99.8 | 94 | n-hexane | 25 | 30 | 96.6 |
| (c) | 96.0 | 99.7 | 92 | n-butanol | 25 | 30 | 96.3 |
| (d) | 90.4 | 99.9+ | 90 | n-hexane | 20 | 30 | 94.2 |
| (e) | 90.4 | 99.9+ | 91 | n-butanol | 20 | 30 | 93.8 |
| (f) | 90.4 | 99.9+ | 70 | Toluene | 20 | 30 | 95.1 |

*Weight % of desired product in the crude material.

3. centrifuging the mixture to permit the formation of three phases, i.e., a solid crystalline phase, an aqueous liquid phase, and a mother liquor phase, said aqueous liquid phase having sufficient height to completely separate the crystalline and mother liquor phases; and 4. separating the crystals from step (3) without contact between the crystals and mother liquor.

* * * * *

UNITED STATES PATENT AND TRADEMARK OFFICE
CERTIFICATE OF CORRECTION

PATENT NO. : 4,079,087
DATED : March 14, 1978
INVENTOR(S) : Yun Chung Sun

It is certified that error appears in the above-identified patent and that said Letters Patent are hereby corrected as shown below:

Column 1, line 7, after the word "always" insert -- easily --.

Column 2, line 13, delete "alkylsubstituted" and insert -- alkyl-substituted --.

Column 4, line 51, after the word "both" insert -- (a) --.

Column 4, line 52, after the word "and" insert -- (b) --.

Signed and Sealed this

Twenty-second Day of August 1978

[SEAL]

Attest:

RUTH C. MASON
Attesting Officer

DONALD W. BANNER
Commissioner of Patents and Trademarks